(12) United States Patent
Williams

(10) Patent No.: US 9,987,145 B2
(45) Date of Patent: Jun. 5, 2018

(54) LATERAL BLOCK PLATE

(71) Applicant: Seth Kevin Williams, Madison, WI (US)

(72) Inventor: Seth Kevin Williams, Madison, WI (US)

( * ) Notice: Subject to any disclaimer, the term of this patent is extended or adjusted under 35 U.S.C. 154(b) by 0 days. days.

(21) Appl. No.: 15/280,684

(22) Filed: Sep. 29, 2016

(65) Prior Publication Data

US 2017/0095344 A1    Apr. 6, 2017

Related U.S. Application Data

(60) Provisional application No. 62/235,643, filed on Oct. 1, 2015.

(51) Int. Cl.
*A61F 2/44* (2006.01)
*A61F 2/30* (2006.01)

(52) U.S. Cl.
CPC .... *A61F 2/447* (2013.01); *A61F 2002/30433* (2013.01); *A61F 2002/30509* (2013.01); *A61F 2002/30578* (2013.01); *A61F 2002/30604* (2013.01); *A61F 2002/30787* (2013.01); *A61F 2002/4475* (2013.01); *A61F 2220/0008* (2013.01)

(58) Field of Classification Search
CPC ....................................................... A61F 2/447
See application file for complete search history.

(56) References Cited

U.S. PATENT DOCUMENTS

| | | | |
|---|---|---|---|
| 2009/0210062 A1* | 8/2009 | Thalgott | A61F 2/4465 623/17.16 |
| 2011/0251689 A1* | 10/2011 | Seifert | A61F 2/442 623/17.16 |
| 2011/0301713 A1* | 12/2011 | Theofilos | A61F 2/447 623/17.16 |
| 2013/0238095 A1* | 9/2013 | Pavento | A61B 17/7059 623/17.16 |
| 2015/0100126 A1* | 4/2015 | Melkent | A61F 2/4455 623/17.16 |
| 2016/0242925 A1* | 8/2016 | Terrell | A61F 2/447 |

* cited by examiner

*Primary Examiner* — Zade Coley
*Assistant Examiner* — Olivia C Chang
(74) *Attorney, Agent, or Firm* — Bell & Manning, LLC

(57) ABSTRACT

A spine stabilization and fusion system includes a lateral cage and a lateral block plate. The lateral cage is configured to be placed between an upper vertebra and a lower vertebra, and a face of the lateral cage includes one or more first holes configured to receive fasteners and a first shaft bore configured to receive a shaft. The lateral block plate includes one or more second holes extending from a lateral face of the lateral block plate to a medial face of the lateral block plate and configured to receive the fasteners. The one or more second holes are configured to align with the one or more first holes of the lateral cage. The lateral block plate also includes a second shaft bore configured to receive the shaft, where the second shaft bore is configured to align with the first shaft bore of the lateral cage.

13 Claims, 11 Drawing Sheets

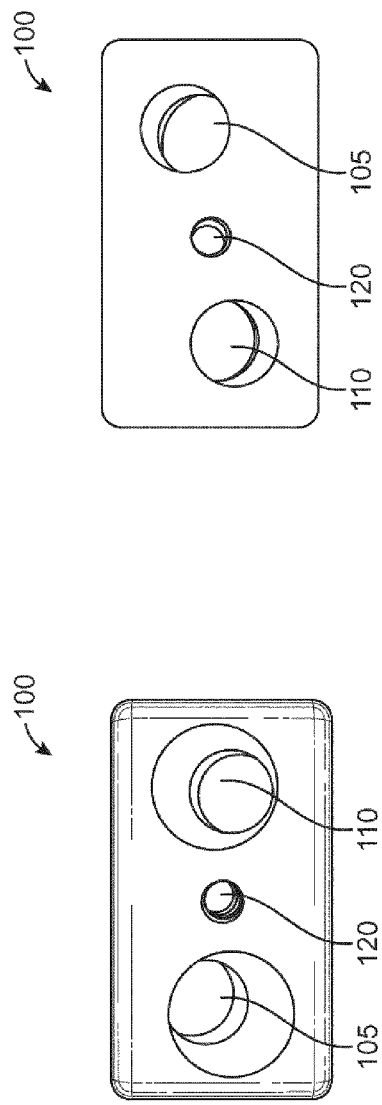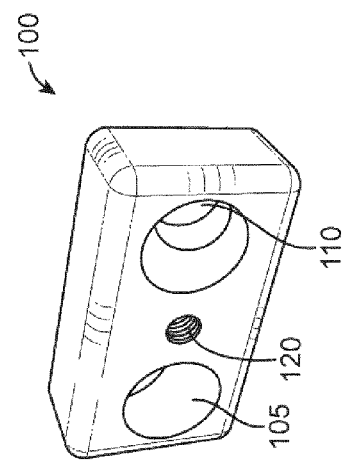

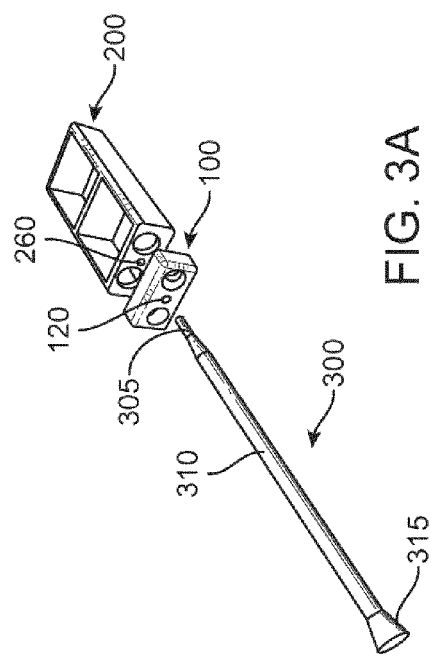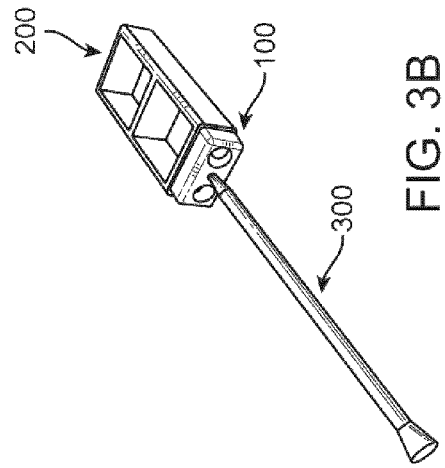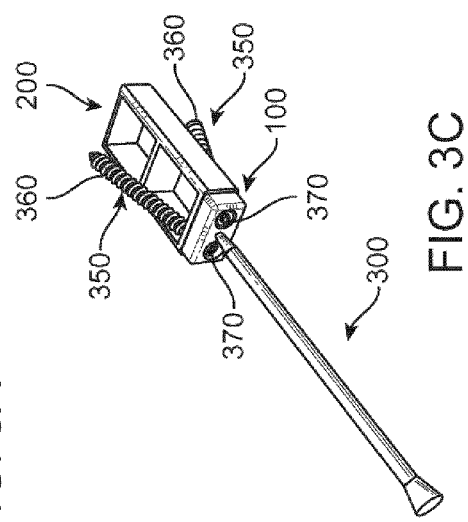

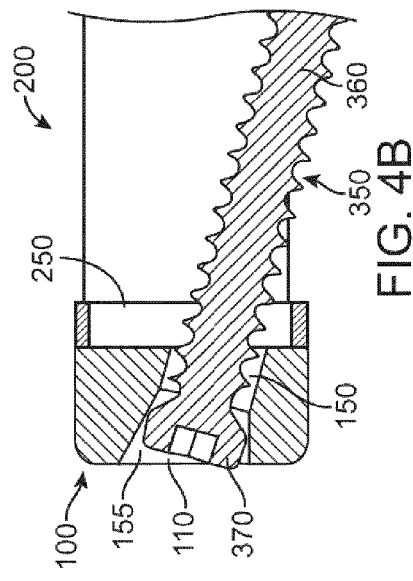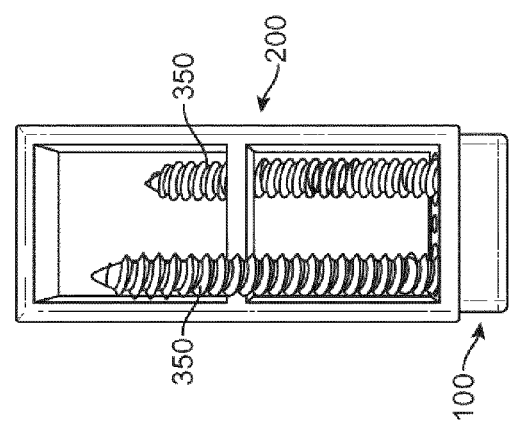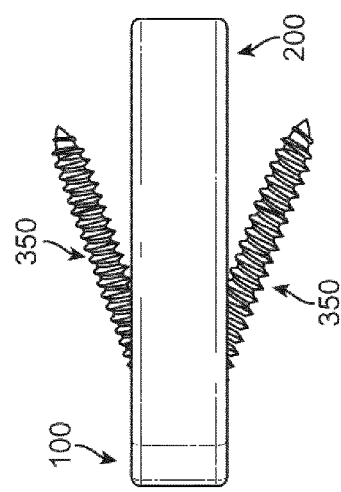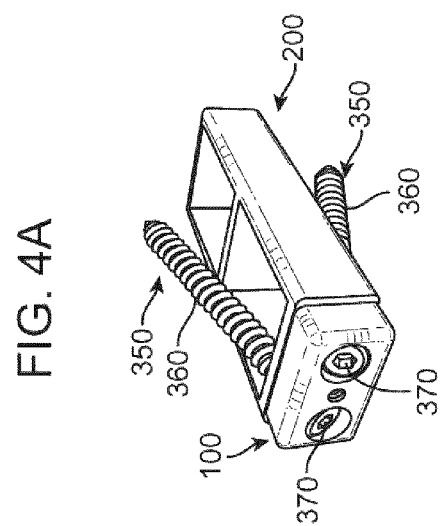

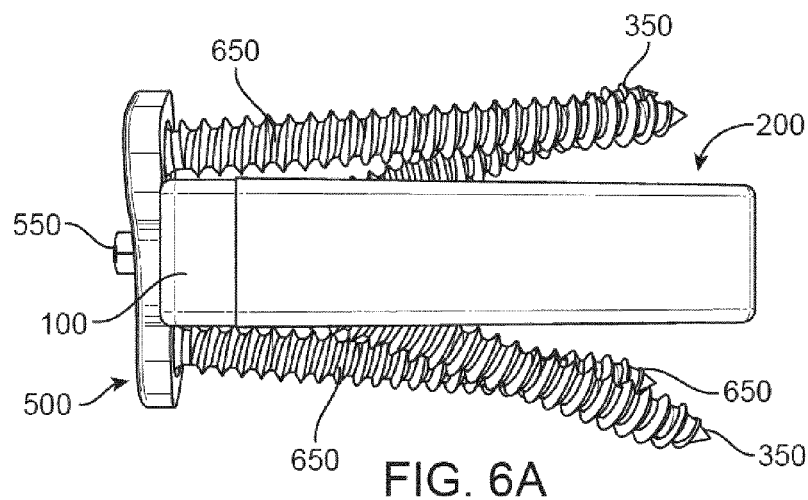
FIG. 6A
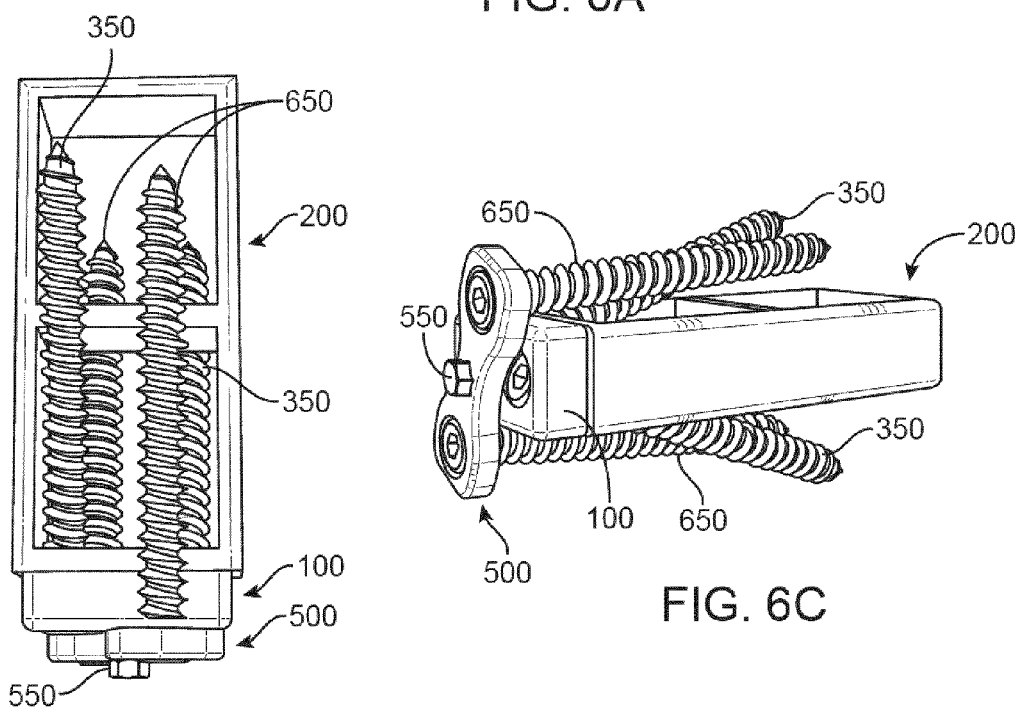
FIG. 6B
FIG. 6C
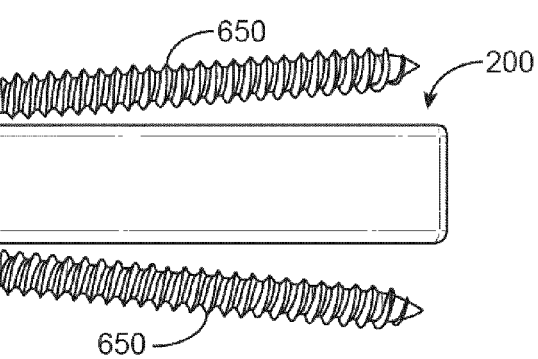
FIG. 6D

LATERAL BLOCK PLATE

CROSS-REFERENCE TO RELATED APPLICATIONS

The present application claims the priority benefit of U.S. Provisional App. No. 62/235,643 filed on Oct. 1, 2015, the entire disclosure of which is incorporated herein by reference.

BACKGROUND

Lumbar spine fusion, or arthrodesis, is a surgical procedure that is performed to fuse two or more vertebrae together. During the procedure, a surgeon places a bone graft or other biological and/or scaffold material that is intended to promote new bone growth between two or more vertebrae. One form of fusion involves removing the majority of the intervertebral disk and replacing the disk with a structural cage that holds bone graft or other material. The spine segments being fused may be stabilized with spinal instrumentation such as a plate and screws. This type of fusion can be performed through a direct lateral or anterolateral retroperitoneal surgical approach. Spinal fusion surgery can be used to relieve nerve generated pain, and to treat ailments such as lumbar degenerative disk disease, spinal stenosis, lumbar spondylolisthesis, and scoliosis.

SUMMARY

An illustrative spine stabilization and fusion system includes a lateral cage and a lateral block plate. The lateral cage is configured to be placed between an upper vertebra and a lower vertebra, and a face of the lateral cage includes one or more first holes configured to receive fasteners and a first shaft bore configured to receive a shaft. The lateral block plate includes one or more second holes extending from a lateral face of the lateral block plate to a medial face of the lateral block plate and configured to receive the fasteners. The one or more second holes are configured to align with the one or more first holes of the lateral cage. The lateral block plate also includes a second shaft bore configured to receive the shaft, where the second shaft bore is configured to align with the first shaft bore of the lateral cage.

A method for spine stabilization and fusion includes placing a lateral cage into a disk space between an upper vertebra and a lower vertebra. A face of the lateral cage includes one or more first holes configured to receive fasteners and a first shaft bore configured to receive a shaft. The method also includes placing a lateral block plate adjacent to the lateral cage. The lateral block plate includes one or more second holes extending from a lateral face of the lateral block plate to a medial face of the lateral block plate and configured to receive the fasteners. The lateral block plate also includes a second shaft bore configured to receive the shaft. The method further includes placing the fasteners through the one or more second holes of the lateral block plate, through the one or more first holes of the lateral cage, and into endplates of the upper vertebra and the lower vertebra.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIGS. 1A-1C depict a lateral block plate in accordance with an illustrative embodiment.

FIG. 3A depicts an insertion handle, a lateral block plate, and a lateral cage in a disassembled configuration in accordance with an illustrative embodiment.

FIG. 3B depicts an insertion handle, a lateral block plate, and a lateral cage in an assembled configuration in accordance with an illustrative embodiment.

FIG. 3C depicts an insertion handle, a lateral block plate, and a lateral cage in an assembled configuration, with screws placed through and engaging the lateral block plate and passing freely through a wall of the lateral cage, in accordance with an illustrative embodiment.

FIG. 4A depicts a front view of a lateral block plate and a lateral cage with screws placed through and engaging the lateral block plate and passing freely through a side wall of the lateral cage, in accordance with an illustrative embodiment.

FIG. 4B is a frontal cross sectional view of a lateral block plate and a lateral cage with screws placed through a lateral cage and passing freely through a side wall of the lateral cage, with a screw head engaging the lateral block plate, in accordance with an illustrative embodiment.

FIGS. 4C and 4D are angled and top views, respectively, of a lateral block plate and screws adjacent to a lateral cage as depicted in FIG. 4A.

FIG. 5B shows a lateral plate in a straight configuration, whereas FIG. 5C shows a lateral plate in an angled configuration.

FIGS. 6A-6C depict a front view, a top view, and an angled view, respectively, of a lateral block plate and screws adjacent to a lateral cage, as well as a lateral plate that is attached to a lateral block plate, with screws now placed through and engaging the lateral plate, in accordance with an illustrative embodiment.

FIG. 6D depicts a front view of a lateral cage with a lateral plate, without the lateral block plate, with screws engaging the lateral plate, in accordance with an illustrative embodiment.

DETAILED DESCRIPTION

Figure 2:
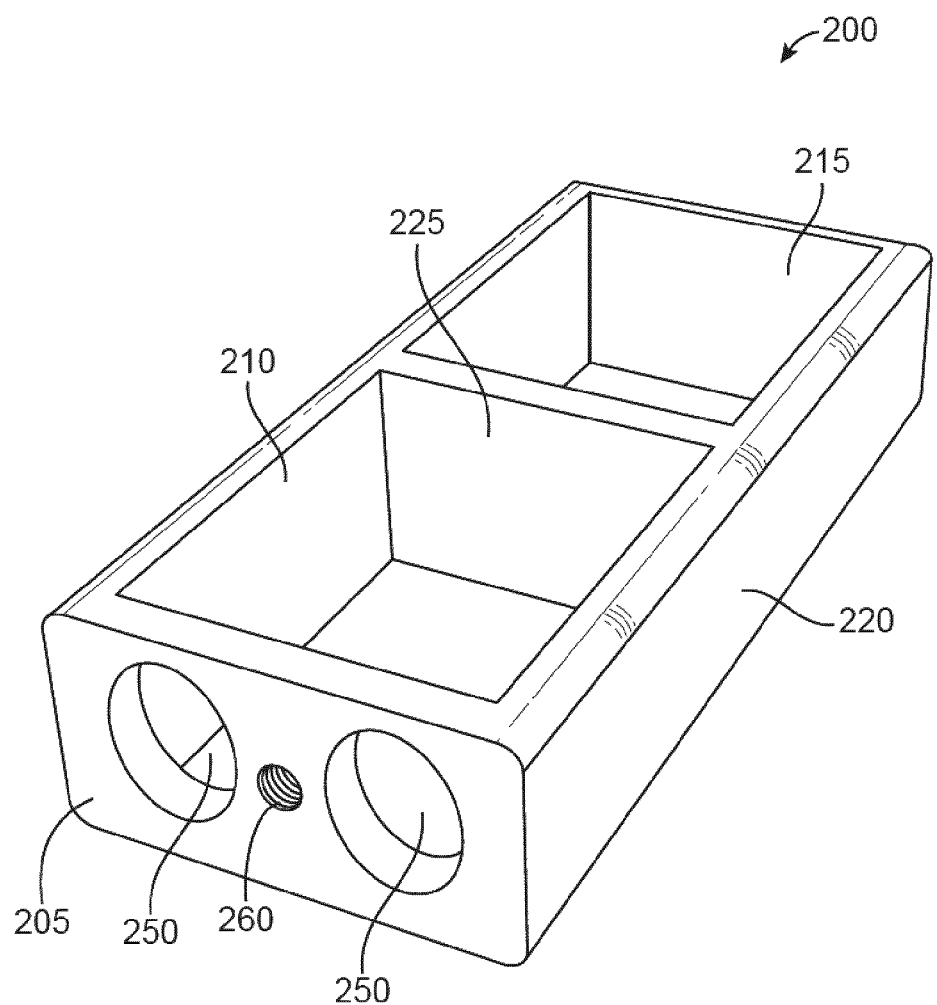
FIG. 2 depicts a lateral cage in accordance with an illustrative embodiment.

The following detailed description is of the best currently contemplated modes of carrying out exemplary embodiments of the subject matter described herein. The description is not to be taken in a limiting sense, but is made merely for the purpose of illustrating the general principles of the described subject matter, since the scope of the subject matter is best defined by the appended claims.

Spinal fusion procedures can be performed via several different approaches, including the lateral retroperitoneal approach or anterolateral retroperitoneal approach. Regardless of the approach used, traditional interbody spinal fusion procedures involve removal and replacement of an intervertebral disk with a cage that is used to provide structural support to the patient in place of the removed disk. The cage usually holds bone graft or other material that promotes a bony fusion, and typically fills some or all of the space that was previously occupied by the removed disk. The cage may be held in place and stabilized by a plate that is mounted outside of the disk space in a vertical position that is substantially perpendicular to both the disk space and the cage. The plate is secured by screws bored into the lateral sides of vertebral bodies above and below the disk space. As such, in traditional procedures, the plate is mounted to the sides of the vertebrae and sits outside the disk space with the screws penetrating the lateral vertebral body cortex, as opposed to sitting partially or completely within the disk space with the screws penetrating the endplates of the vertebrae.

Such spinal fusion techniques are prone to several problems due in part to the position in which the plate is mounted to the vertebral bodies. The psoas muscle and lumbar nerve plexus both run along the lateral sides of the vertebral bodies in the lumbar portion of the spine, making it difficult for the surgeon to properly place the vertical plate without interfering with one or both of the psoas muscle and the lumbar nerve complex. It can be difficult to hold the plate in position on the vertebral body while drilling the screw holes, as the force of the drill guide and the action of the drill on the hard vertebral bone have a tendency to cause the plate to migrate cephalad or caudal during drilling. Additionally, even when the surgeon is able to successfully place the plate, conventional plates may be prominent and can cause irritation to the psoas muscle and/or the lumbar nerve plexus. Another issue is the presence of pedicle screws in the vertebral body below or caudal to the fusion in cases where a patient has had a previous instrumented spinal fusion and now has developed adjacent segment deterioration above or cephalad to the previous fusion. In this situation it can be difficult to place a screw through a plate because the new screw trajectory often overlaps with the existing screw, and the surgeon is forced to place a longer plate than desired in order to allow for new screw placement below or cephalad to the existing screws. In view of these problems, the inventor has designed a new system that utilizes a cage in conjunction with a plate that may be positioned entirely or predominantly within the disk space. Additionally, the new system uses a plate or plates that are initially attached to the cage, which holds the plate or plates firmly in position so there is no plate movement during drilling, and then the plate or plates are detached from the cage to allow for separate biomechanical forces on the cages and plate or plates during patient activity.

Broadly, the embodiments described herein provide a spinal fusion plate that may be placed within the intervertebral space along with a cage in lateral and anterolateral spinal fusion procedures. Another lateral plate can be attached to the intervertebral plate, or can be used primarily, to provide additional options of achieving spinal stability. The spinal plates described herein solve the problems of traditional systems with plate placement and plate prominence and screw placement above a previous instrumented fusion because it can sit within the disk space, rather than outside the disk space. The system also solves the problem of plate migration during drilling because the plate or plates are initially attached to the lateral cage during the drilling and screw placement process.

FIG. 1A depicts a lateral or side view of a lateral block plate 100, in accordance with an illustrative embodiment. It is called a lateral block plate because in at least one embodiment it is shaped like a rectangular block. The lateral block plate 100 may be provided in different heights, such as in 1 millimeter (mm) increments starting at approximately 5 mm up to about 20 mm, depending on the thickness of the cage and the vertical dimensions of the intervertebral space to be filled. The lateral block plate 100 may have the same height anteriorly and posteriorly, or it can be configured to be taller anteriorly than posteriorly, thus reproducing or restoring a patient's lumbar lordosis. The plate width (i.e., the distance between the most lateral aspect of the plate and the most medial aspect of the plate) is selected to be between about 3-8 mm, preferably on the order of 5 mm. The lateral block plate length (i.e., the distance between the most posterior aspect of the plate and the most anterior aspect of the plate) can depend on the width of the cage, the width of the vertebrae to be fused, and/or the number of screw holes (e.g., 2, 3, or 4) to be used to secure the lateral block plate, and may be between about 15 mm-25 mm, preferably on the order of 20 mm. In alternative embodiments, different dimensions may be used for the height, width, and/or length of the lateral block plate. The lateral block plate 100 can be made with various materials, including titanium, titanium alloy, polyether ether ketone (PEEK), or a carbon fiber/PEEK combination. These are all existing materials that are commonly used for the manufacture of implanted medical devices. The lateral block plate is manufactured using existing manufacturing methods and standards that are currently used in the manufacture of medical implants. It should be understood, of course, that the foregoing relates to exemplary embodiments and that modifications may be made without departing from the spirit and scope of the invention as set forth in the claims.

Holes 105 and 110 accommodate screws or fasteners that pass through the lateral block plate 100 to secure it to bone. In an alternative embodiment, a lateral block plate may include more than two holes to accommodate screws or fasteners. In an illustrative embodiment, hole 105 is angled upwards between 10 and 25 degrees and hole 110 is angled downwards between 10 and 25 degrees. In alternative embodiments, different angles may be used for the holes 105 and 110. Holes 105 and 110 are tapered to allow for passage of a threaded screw shaft (shown later) through the plate with screw head engagement of the plate without the screw head being prominent. Hole 120 is threaded and accommodates an insertion handle or a bolt to attach a lateral plate (shown later) to a lateral block plate 100. In an alternative embodiment, hole 120 may not be threaded, but may be designed to accommodate a fastener that will attach to a lateral plate (shown later).

FIG. 1B depicts a back side view of a lateral surface of a lateral block plate 100, in accordance with an illustrative embodiment. Holes 105 and 110 accommodate screws or fasteners that pass through the lateral block plate to secure it to bone. Hole 105 is angled upwards between 10 and 25 degrees and hole 110 is angled downwards between 10 and 25 degrees. Hole 120 is threaded and accommodates an insertion handle or a bolt to attach a lateral plate to the lateral block plate. In an alternative embodiment, hole 120 may not be threaded, but may be designed to accommodate a fastener that will attach to a lateral plate (shown later). FIG. 1C depicts an angled view of a lateral block plate 100, in accordance with an illustrative embodiment. Holes 105 and 110 accommodate screws or fasteners that pass through the lateral block plate to secure it to bone. Hole 105 is angled upwards between 10 and 25 degrees and hole 110 is angled downwards between 10 and 25 degrees. Hole 120 is threaded and accommodates an insertion handle or a bolt to attach a lateral plate to the lateral block plate. In an alternative embodiment, hole 120 may not be threaded, but may be designed to accommodate a fastener that will attach to a lateral plate (shown later).

FIG. 2 depicts an angled view of a structural fusion cage 200, also called a lateral cage 200, that is designed to be inserted into the intervertebral space after a discectomy is performed via a retroperitoneal direct lateral or anterolateral approach, in accordance with an illustrative embodiment. A lateral cage may be comprised of walls 205, 210, 215, 220, and 225, or in an alternative embodiment, may be compromised of more or fewer walls. Wall 215 is the leading edge of the lateral cage 200, in that it is inserted first into the disk space, and faces laterally, opposite the surgical wound. Wall 205 is opposite wall 215 and faces lateral towards the surgical wound and is the only visible part of the cage to the surgeon once it is inserted in the disk space. As an example, if cage 200 was inserted via a right-sided direct lateral surgical approach, wall 215 would be the leading edge of insertion and would therefore face the left side of the patient's body, and wall 205 would face the right side of the patient's body, and would be visible from the surgical wound. While the dimensions of the cage may vary, it is estimated that the height will vary between approximately 6 mm and 20 mm, the length (the distance from wall 205 to wall 215, inclusive) will vary between approximately 35 mm and 60 mm, and the width (the distance from wall 210 to 220, inclusive) will vary between approximately 15 mm and 25 mm. Hole 260 is threaded and accommodates an insertion handle or a bolt to attach a lateral plate (shown later) to the lateral block plate. In an alternative embodiment, hole 260 may not be threaded, but may be designed to accommodate a fastener that will attach to a lateral plate (shown later). Holes 250 are designed to allow free passage of screws or fasteners that will be placed through a lateral block plate 100 to secure a lateral block plate 100 to a vertebral body or bodies. In an alternative embodiment, holes 250 may be located eccentrically in a cephalad or caudal direction in wall 205, such that holes 250 are completely open in a cephalad or caudal direction, to allow for free passage of screws or fasteners.

FIG. 3A depicts a disassembled angled view of the lateral cage 200, the lateral block plate 100, and an insertion handle 300, in accordance with an illustrative embodiment. Insertion handle 300 has a threaded leading end 305 that threads into lateral block plate 100 through threaded hole 120 and through lateral cage 200 through threaded hole 260. Insertion handle 300 has a shaft portion 310 of variable length and a back end 315 of variable configuration. Alternative embodiments of insertion handle 300 could have a variety of mechanisms to connect to lateral block plate 100 and lateral cage 200 rather than through a threaded terminal end 305 and threaded holes 120 and 260.

FIG. 3B depicts an assembled angled view of a lateral cage 200, a lateral block plate 100, and an insertion handle 300, in accordance with an illustrative embodiment. The lateral block plate 100 is securely held to lateral cage 200 through their connection to insertion handle 300, and can now be inserted into an intervertebral disk space as part of the fusion operation. Once inserted into the intervertebral disk space, screws 350 with a threaded shaft portion 360 and head portion 370 can be placed through lateral block plate 100 and lateral cage 200 to engage the vertebral bodies above and below the lateral cage 200, as depicted in FIG. 3C. The screw threaded shaft portion 360 will pass freely through the holes 105 and 110 (not shown here, shown in FIGS. 1A-1C) in the lateral block plate 100 and through the holes 250 (not shown) in the lateral cage 200, whereas the screw head portion 370 when fully inserted will engage the lateral block plate 100 and securely hold the lateral block plate 100 in place in the intervertebral space (shown later). In an alternative embodiment, fasteners other than screws 350 may be used to secure the lateral block plate 100 and the lateral cage 200 to the vertebral bodies.

FIG. 4A depicts a front view of the lateral block plate 100 and the lateral cage 200 with screws 350 placed through and engaging the lateral block plate 100 and passing freely through a side wall of the lateral cage 200, in accordance with an illustrative embodiment. Screws 350 are inserted into the vertebral bodies above and below the disk space being fused. Screws 350 are approximately 4 mm to 6 mm in diameter and between 20 mm and 60 mm in length. Provided the lateral block plate 100 is seated entirely or partially within the disk space, screws 350 enter the endplates of the vertebral bodies above and below the disk space being fused and are anchored in the cancellous vertebral body bone. If the lateral block plate is positioned more lateral, screws 350 may enter the lateral cortex of the vertebral bodies above and below the disk space being fused. The screw pathways may be established with a drill or an awl prior to insertion of screws 350. The rigid connection of the lateral block plate to the lateral cage via the insertion handle (not shown) prevents cage migration during screw pathway drilling and screw placement. In an alternative embodiment, fasteners other than screws may be used to secure a lateral block plate 100 to a vertebral body. Insertion handle 300 (not shown) has been removed after screw insertion.

FIG. 4B is a frontal cross sectional view of a lateral block plate 100 and a lateral cage 200 with screw 350 placed through hole 110 in lateral block plate 100 and passing freely through hole 250 in a side wall of lateral cage 200, in accordance with an illustrative embodiment. Screw 350 is comprised of a threaded shaft portion 360 and a head portion 370. Hole 110 is tapered and has a larger diameter portion 155 that accommodates head portion 370, allowing the head portion 370 to seat fully or nearly-fully within lateral block plate 100 once inserted; and hole 110 has a smaller diameter portion 150 that is slightly larger than and allows free passage of threaded shaft portion 360 but is smaller than head portion 370. When screw 350 is inserted fully, head portion 370 tightly presses up against the smaller diameter portion 150 of hole 110, this securing the lateral block plate 100 to bone. FIG. 4C is an angled view of a lateral block plate 100 and screws 350 with screw heads 370 and threaded screw shafts 360, with the lateral block plate 100 adjacent to a lateral cage 200 as depicted in FIG. 4A and FIG. 4B, in accordance with an illustrative embodiment. FIG. 4D is top view of a lateral block plate 100 and screws 350 adjacent to a lateral cage 200 as depicted in FIGS. 4A and 4B, in accordance with an illustrative embodiment.

Figure 5B:
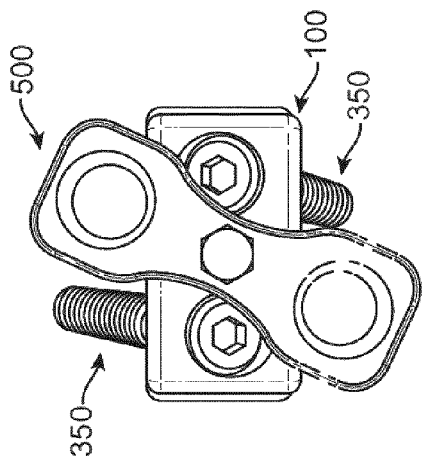
FIG. 5B depicts an angled view of a lateral block plate and screws adjacent to a lateral cage, as well as a lateral plate that is attached to the lateral block plate with a bolt, in accordance with an illustrative embodiment.
Figure 5D:
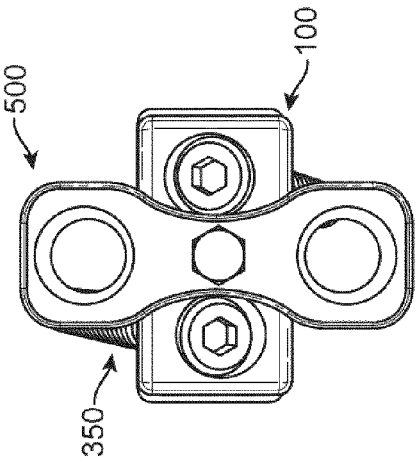
FIGS. 5C and 5D depict a side view of a lateral block plate and screws adjacent to a lateral cage, as well as a lateral plate that is attached to the lateral block plate, in accordance with an illustrative embodiment.
Figure 5A:
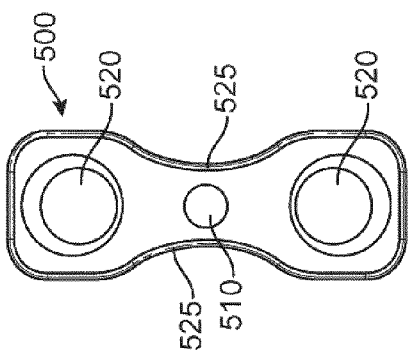
FIG. 5A depicts a side view of a lateral plate in accordance with an illustrative embodiment.

FIG. 5A depicts a side view of a lateral plate 500 with a tapered waist 525 and with a central hole 510 and eccentric holes 520, in accordance with an illustrative embodiment. Holes 520 allow for bone screws or fasteners to be placed for securing the lateral plate to bone. Central hole 510 allows for passage of a threaded bolt (550 shown in FIG. 5B) to connect the lateral plate 500 to a lateral block plate, or to allow for an insertion handle (shown in FIGS. 3A-3B) to engage a lateral plate 500, a lateral block plate 100, and a lateral cage 200 (shown in FIG. 5B) such that they can be inserted as a single unit prior to screw placement. Another option is for the surgeon to engage a lateral plate 500 with an insertion handle in order to hold it rigidly in place during screw pathway drilling and screw placement. In an alternative embodiment, a lateral plate 500 may not have a tapered waist and so may be shaped in a more rectangular manner and may include 3, 4, or more holes to accommodate bone screws or fasteners, and may be secured to a lateral block plate by a mechanism other than a bolt. The lateral plate 500 can be made with various materials, including titanium, titanium alloy, polyether ether ketone (PEEK), or a carbon fiber/PEEK combination. These are all existing materials that are commonly used for the manufacture of implanted medical devices. The lateral plate is manufactured using existing manufacturing methods and standards that are currently used in the manufacture of medical implants. It should be understood, of course, that the foregoing relates to exemplary embodiments and that modifications may be made without departing from the spirit and scope of the invention as set forth in the claims.

Figure 5C:
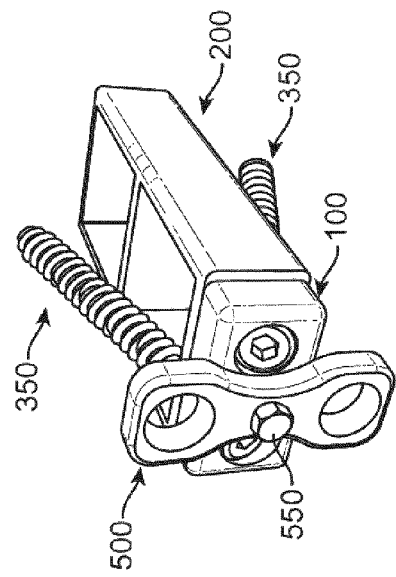

FIG. 5B depicts an angled view of the lateral block plate 100 and screws 350 adjacent to the lateral cage 200 as well as a lateral plate 500 that is attached to the lateral block plate 100 via bolt 550, in accordance with an illustrative embodiment. Bolt 550 is an optional feature that can be passed through central hole 510 as depicted in FIG. 5A, and would be placed after removal of the insertion handle (not shown) per the surgeon's discretion. Bolt 550, if used, would mate the lateral plate 500 to the lateral block plate 100 but would not mate to the lateral cage 200. In an alternative embodiment, the bolt 550 can also be used to mate the lateral plate 500 to the lateral block plate 100 and to the lateral cage 200. FIGS. 5C and 5D depict a side view of the lateral block plate 100 and screws 350 adjacent to the lateral cage 200, as well as the lateral plate 500 that is attached to the lateral block plate 100 via bolt 550, in accordance with illustrative embodiments. FIG. 5C shows a side view of the lateral plate 500 in a straight configuration, whereas FIG. 5D shows a side view of the lateral plate 500 in a rotated configuration. The lateral plate 500 can be placed and rotated at any angle with respect to lateral block plate 100, provided the screw pathway does not overlap with the face of the lateral block plate. When the lateral plate 500 is positioned straight as in FIG. 5C, if the plate is designed with a tapered waist as depicted in FIGS. 5A and 5C, the screws 350 can be placed or accessed with the lateral plate 500 in place. The lateral plate 500 could then be rotated as depicted in FIG. 5D. When the lateral plate 500 is positioned rotated as in FIG. 5D, if the plate is designed with a tapered waist as depicted in FIG. 5A, the screws 350 are held in a locked position in that they are prevented from backing out due to the overlapping of plate 500 with the screw heads of screws 350.

FIG. 6A depicts a front view of the lateral block plate 100 with screws 350 adjacent to the lateral cage 200, as well as the lateral plate 500 that is attached to the lateral block plate 100 via bolt 550, with screws 650 now passing through and engaging the lateral plate 500, in accordance with an illustrative embodiment. Screws 650 have the same general configuration as screws 350, with a threaded shaft 360 as depicted in FIG. 4B and a screw head 370 that engages a plate as depicted in FIGS. 4B and 4C. Though similar in configuration, screws 650 are separately identified from screws 350 in this description to distinguish them from screws 350. The primary difference between screws 650 and screws 350 is that screws 350 pass through and engage via the screw head the lateral block plate 100 whereas screws 650 pass through and engage via the screw head the lateral plate 500. Hence in this description, the fundamental difference between the screw 350 and the screw 650 is not necessarily the physical dimensions of the screw, but the plate with which they are associated. Screws 350 are associated with the lateral block plate 100 and screws 650 are associated with the lateral plate 500. Screws 350 and screws 650 may have different dimensions depending on surgeon preference. FIG. 6B depicts a top view and FIG. 6C depicts an angled view of the lateral block plate 100 with screws 350 adjacent to the lateral cage 200, as well as the lateral plate 500 that is attached to the lateral block plate 100 via bolt 550, with screws 650 now passing through and engaging the lateral plate 500, in accordance with illustrative embodiments.

FIG. 6D depicts a front view of the lateral plate 500 adjacent to the lateral cage 200 with screws 650 passing through and engaging the lateral plate 500, in accordance with an illustrative embodiment. In an alternative embodiment, lateral plate 500 could be designed to accommodate more than two screws 650, the most common configuration likely being a total of four screws. In the configuration depicted in FIG. 6D, the surgeon has elected to not use a lateral block plate 100 as seen in FIGS. 6A-6C. The lateral plate 500 is initially secured to the lateral cage 200 via an insertion handle (not shown) in a manner similar to the assembly steps depicted in FIGS. 3A-3C, except in the method used as depicted in FIG. 6D the insertion handle engages the lateral plate 500 and the lateral cage 200, rather than engaging the lateral block plate 100 and the lateral cage 200 as depicted in FIGS. 3A-3C. Once the lateral cage 200 is inserted into the intervertebral space as part of the spinal fusion and the lateral plate 500 rests against the lateral aspects of the vertebral bodies above and below the disk space, the lateral plate 500 is held rigidly in position by virtue of the firm connection of the insertion handle (not shown) to the lateral plate 500 and the lateral cage 200, and the screw holes can be drilled. The advantage to this configuration is the rigid connection of the lateral plate 500 to the lateral cage 200, which due to the lateral cage being firmly seated within the disk space and with further control imparted by the insertion handle, prevents any movement or migration of the plate during screw pathway drilling and screw insertion. In one embodiment, a drill guide can be designed to mate with the insertion handle and rest against the plate, allowing for ease of drilling for the screws. Once screws 650 are placed into the vertebral bodies, the insertion handle (not shown) is removed, thereby completely disengaging a lateral plate 500 from the lateral cage 200, allowing the lateral plate 500 and the lateral cage 200 to be subject to separate biomechanical forces as the spinal column is loaded during patient activity.

Figure 7A:
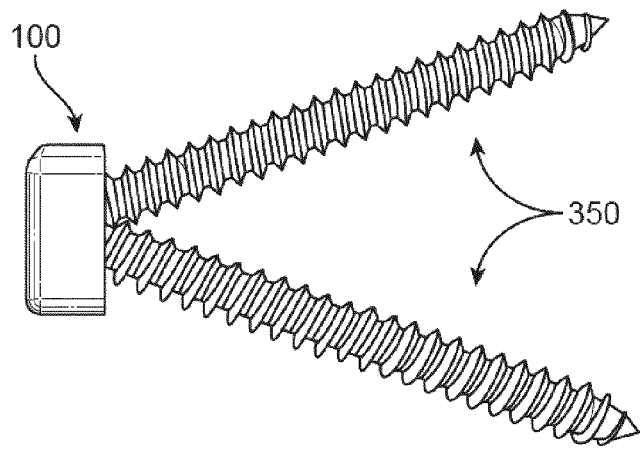
FIGS. 7A-7C depict a front view and two angled views showing the lateral sides of the of a lateral block plate with screws, in accordance with an illustrative embodiment.
Figure 7B:
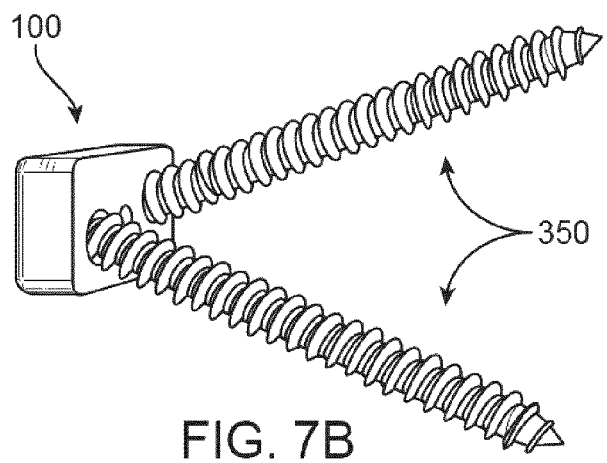
Figure 7C:
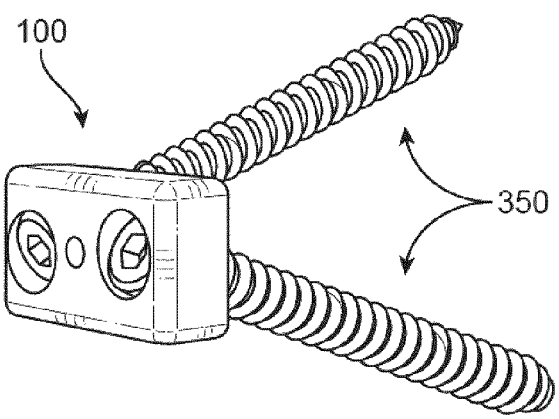

FIG. 7A depicts a front view of the lateral block plate 100 with screws 350, in accordance with an illustrative embodiment. FIGS. 7B and 7C depict angled views of the lateral block plate 100 with screws 350, in accordance with illustrative embodiments. Lateral block plate 100 in FIGS. 7A-7C is depicted without the lateral cage 200 or lateral plate 500 as seen in FIGS. 6A-6C.

Figure 8A:
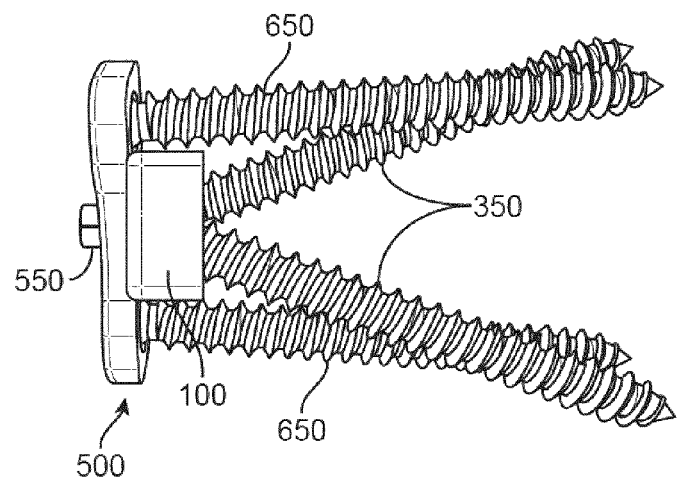
FIGS. 8A-8C depict a front view and two angled views showing the lateral sides of a lateral plate attached to a lateral block plate with screws engaging both plates, in accordance with an illustrative embodiment.
Figure 8B:
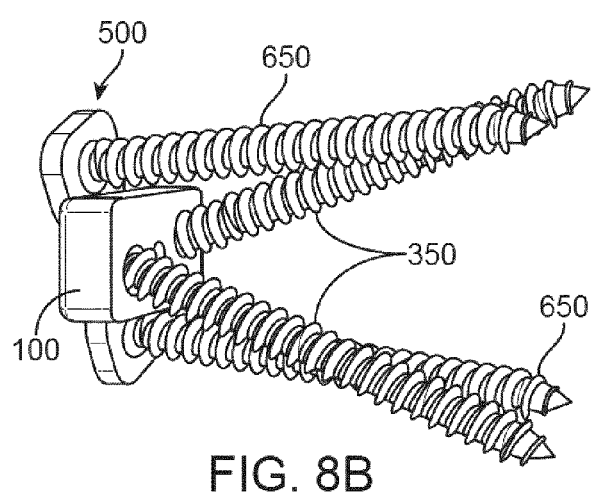
Figure 8C:
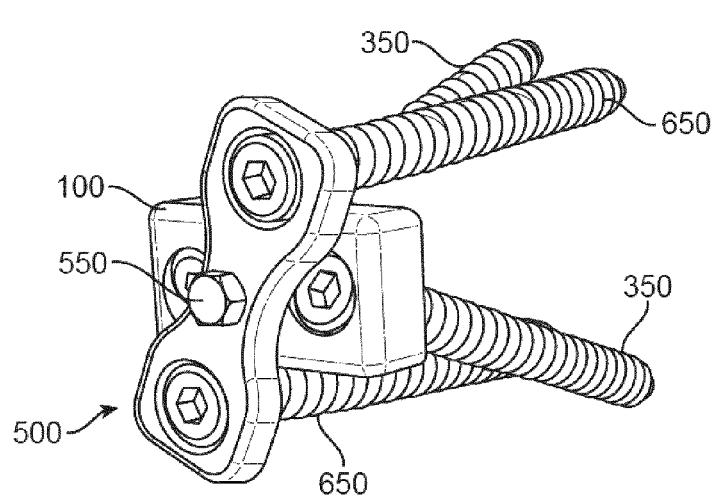

FIG. 8A depicts a front view of the lateral plate 500 attached to the lateral block plate 100 via bolt 550 with screws 650 placed through and engaging the lateral plate 500 and screws 350 placed through and engaging the lateral block plate 100, in accordance with an illustrative embodiment. FIGS. 8B and 8C depict angled views of the lateral plate 500 attached to the lateral block plate 100 via bolt 550 (not shown in FIG. 8B) with screws 650 placed through and engaging lateral plate 500 and screws 350 placed through and engaging lateral block plate 100, in accordance with illustrative embodiments. Lateral block plate 100 and lateral plate 500 in FIGS. 8A-8C are depicted without the lateral cage 200 as seen in FIGS. 6A-6C.

Figure 9:
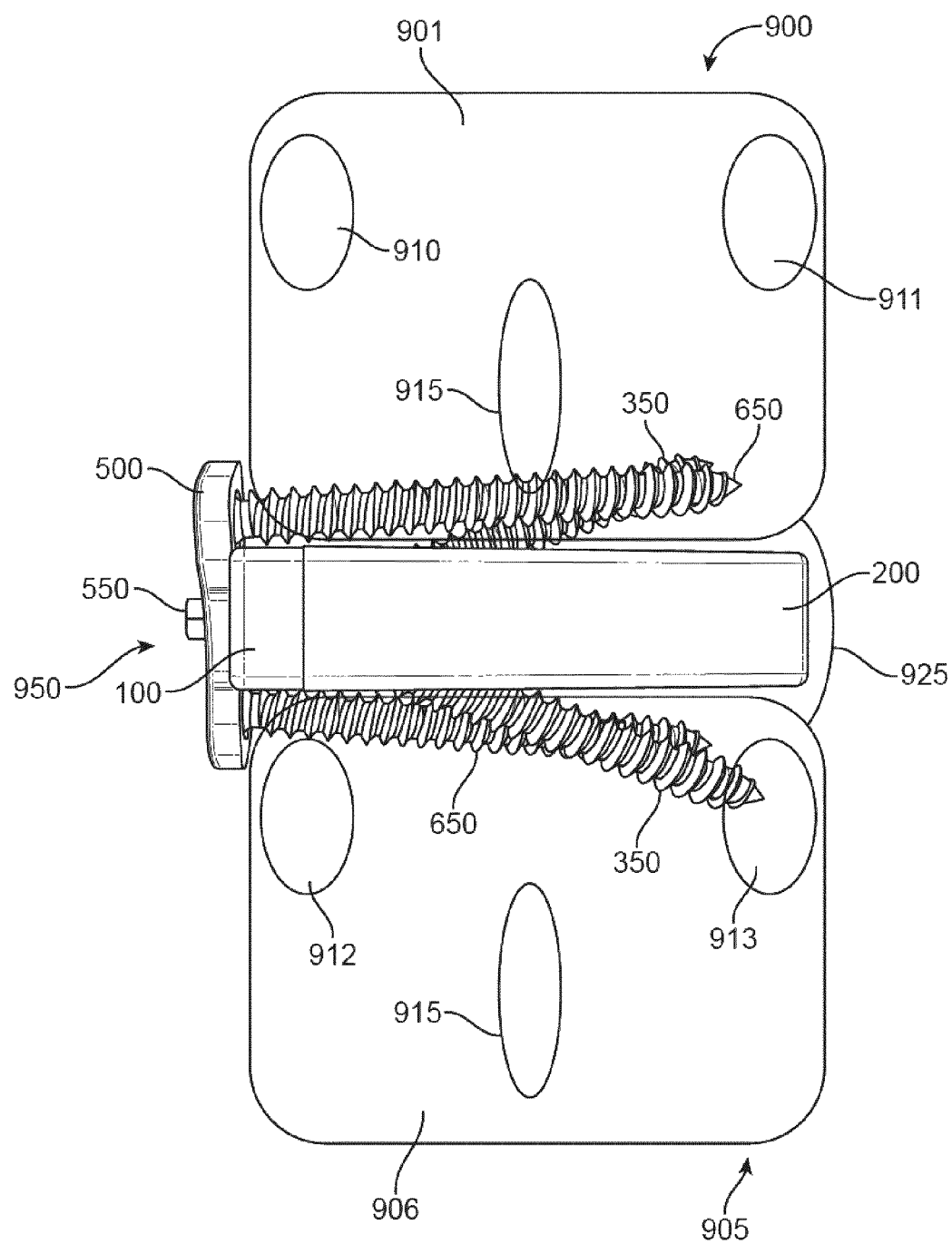
FIG. 9 depicts a front view of a spine segment with a vertebral body above and below a disk space, with the disk space occupied by the lateral block plate and screws adjacent to a lateral cage, as well as a lateral plate and screws, with the screws secured to the vertebral bodies, in accordance with an illustrative embodiment.

FIG. 9 depicts a front view of the lateral block plate 100 with associated screws 350 and the lateral plate 500 with associated screws 650 adjacent to the lateral cage 200 (950 collectively, as shown in FIG. 6A) after insertion into disk space 925 between vertebrae 900 and 905, in accordance with an illustrative embodiment. Vertebrae 900 is above or cephalad to the disk space and includes vertebral body 901 and pedicles 910 and 911 and spinous process 915. Vertebrae 905 is below or caudal to the disk space and includes vertebral body 906 and pedicles 912 and 913 and spinous process 915. The screw 350 inserted into vertebral body 906 passes above or cephalad to pedicle 912, so will pass above or cephalad to a pedicle screw (not shown) that would occupy pedicle 912 from a previous instrumented spinal fusion. The length of screw 350 can be selected to stop short of pedicle 913 if it is occupied with a pedicle screw (not shown) from a previous instrumented spinal fusion. The screw 650 may also be placed in a manner as to avoid a screw occupying pedicle 912.

Figure 10A:
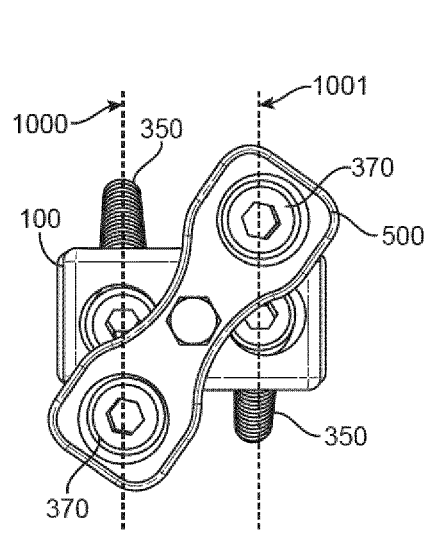
FIGS. 10A and 10B depict a side view and a top view, respectively, of a lateral block plate and a lateral plate and screws adjacent to a lateral cage, with lines drawn to indicate cross sectional planes depicted in FIGS. 10C and 10D, in accordance with an illustrative embodiment.
Figure 10B:
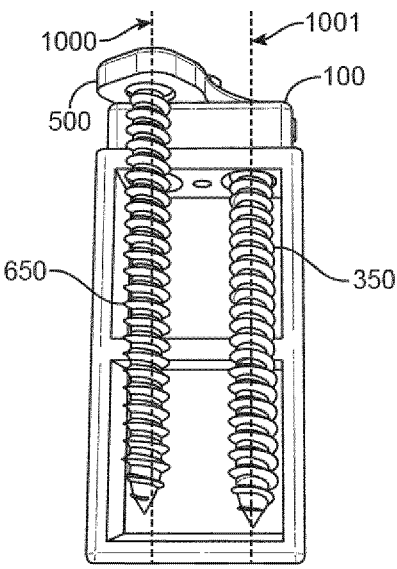
Figure 10C:
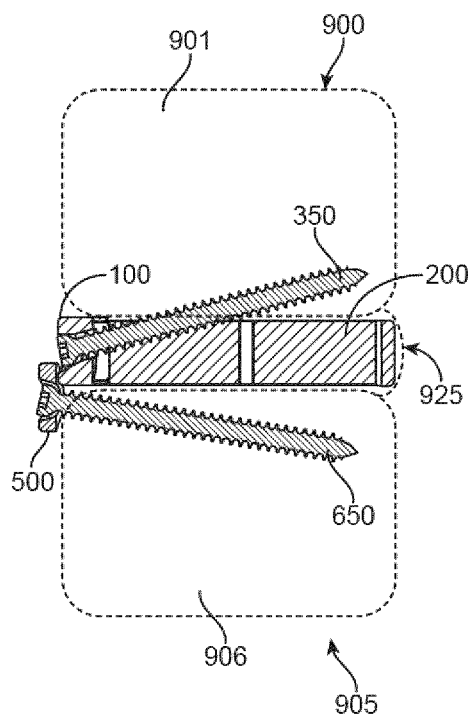
Figure 10D:
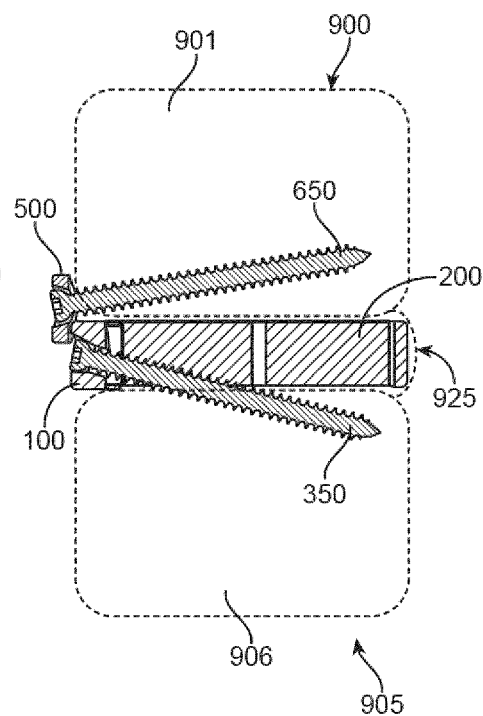

FIG. 10A depicts a side view of the lateral block plate 100 and lateral plate 500 and screws 350, and screw heads 370 of screws 650 (screws 650 not visible due to the angle of view), with lines 1000 and 1001 drawn to indicate cross sectional planes depicted in FIGS. 10C and 10CD respectively, in accordance with illustrative embodiments. FIG. 10B depicts a top view of the lateral block plate 100 with associated screw 350 and the lateral plate 500 with associated screw 650, with lines 1000 and 1001 drawn to indicate cross sectional planes depicted in FIGS. 10C and 10CD respectively, in accordance with illustrative embodiments. In FIG. 10B, screws 650 and 350 overlap, so only a single screw of each 350 and 650 are visible, though there are four screws present as depicted in FIG. 10A. FIG. 10C depicts a cross sectional image through plane 1000 (as shown in FIGS. 10A and 10B) of the lateral cage 200 inserted in a disk space 925 between a vertebrae 900 and a vertebrae 905, with the lateral block plate 100 and the lateral plate 500, in accordance with an illustrative embodiment. The lateral block plate 100 can sit entirely or partially within the disk space 925, or can be positioned outside and lateral to the disk space 925, whereas the lateral plate 500 is always positioned entirely outside a disk space 925. The screw 350 passes through the lateral block plate 100 and lateral cage 200 and is inserted into a vertebral body 901, with the screw head of a screw 350 engaging the lateral block plate 100, thus securing the lateral block plate 100 firmly to the vertebral body 901. The screw 650 passes through the lateral plate 500 and is inserted into the vertebral body 906, with the screw head of the screw 650 engaging the lateral plate 500, thus securing the lateral plate 500 firmly to the vertebral body 906. FIG. 10D depicts a cross sectional image through plane 1001 (as shown in FIGS. 10A and 10B) of the lateral cage 200 inserted in the disk space 925 between the vertebrae 900 and the vertebrae 905, with the lateral block plate 100 and the lateral plate 500, in accordance with an illustrative embodiment. The screw 350 passes through the lateral block plate 100 and the lateral cage 200 and is inserted into the vertebral body 906, with the screw head of the screw 350 engaging the lateral block plate 100, thus securing the lateral block plate 100 firmly to the vertebral body 906. The screw 650 passes through the lateral plate 500 and is inserted into the vertebral body 901, with the screw head of the screw 650 engaging the lateral plate 500, thus securing the lateral plate 500 firmly to the vertebral body 901.

Figure 11:
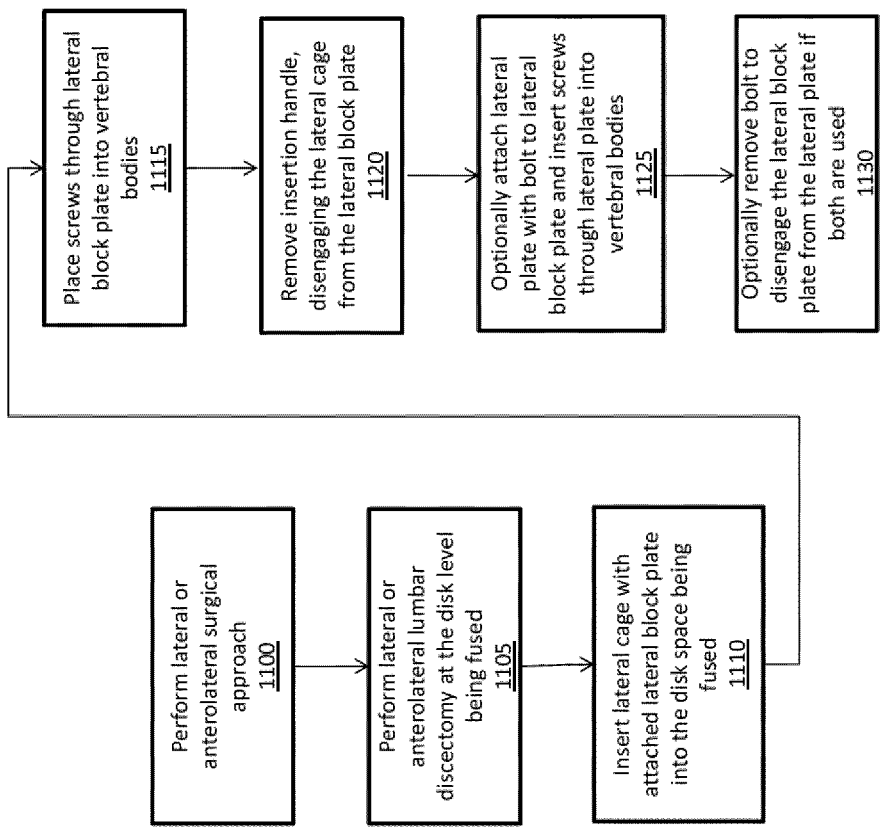
FIG. 11 is a flow diagram depicting a process for performing a lumbar spine fusion with a lateral block plate and/or a lateral plate in accordance with an illustrative embodiment.

FIG. 11 is a flow diagram depicting a process for performing a lumbar spine fusion in accordance with an illustrative embodiment. In alternative embodiments, fewer, additional, and/or different operations may be performed. Additionally, the use of a flow diagram is not meant to be limiting with respect to the order of operations performed.

In an operation 1100, the surgeon makes an incision and performs a retroperitoneal anterolateral or direct lateral approach to access the disk space to be fused in a manner well known to those skilled in the art.

In an operation 1105, the surgeon performs a lateral or anterolateral lumbar discectomy in a manner well known to those skilled in the art, in preparation for performing a fusion.

In an operation 1110, a lateral cage is attached to a lateral block plate via an insertion handle and is inserted into the disk space being fused. In illustrative embodiments, the disassembled lateral cage and lateral block plate and insertion handle are described with reference to FIG. 3A, and the assembled lateral cage and lateral block plate and insertion handle are described with reference to FIG. 3B.

In an operation 1115, the surgeon drills screw holes and places screws through the lateral block plate into the vertebral bodies above and below the disk space being fused. In an illustrative embodiment, the lateral block plate with screws are described with reference to FIG. 3C.

In an operation 1120, the surgeon removes the insertion handle, thus disengaging the lateral block plate from the lateral cage. This could be the conclusion of the fusion operation, or optionally depending on surgeon discretion in an operation 1125, the surgeon may now attach a lateral plate to the lateral block plate with a bolt. This holds the lateral plate rigidly in place to prevent plate migration during subsequent drilling of the screw holes and screw placement. Alternatively the surgeon could use an insertion handle to hold the lateral plate rigidly in place during screw pathway drilling. In an illustrative embodiment, the lateral block plate with screws through and engaging the lateral block plate, as well as the adjacent unattached lateral cage, are described with reference to FIGS. 5B-5D. Screws can now be placed through the lateral plate into the vertebral bodies above and below the disk level to be fused. In an illustrative embodiment, the lateral block plate with screws through and engaging the lateral block plate, and the lateral plate with screws through and engaging the lateral plate, as well as the adjacent unattached lateral cage, are described with reference to FIGS. 6A-6C and FIG. 9.

In an operation 1130, if the surgeon has used both the lateral block plate and the lateral plate and they are attached via a bolt, the surgeon may choose to remove the bolt connecting the lateral block plate to the lateral plate, allowing the lateral block plate with associated screws and the lateral plate with associated screws to be exposed to separate biomechanical forces. The choice of leaving the bolt in place or removing it is based on the clinical circumstances and is up to the discretion of the surgeon. Once the lateral cage, lateral block plate and/or lateral plate, and screws are fully inserted, the surgeon then completes the operation by closing the wound in a manner well known to those skilled in the art.

The components described herein can be made in a variety of lengths and/or shapes to accommodate various patient anatomies and surgeon preferences. The components can be made from stainless steel, titanium, titanium-alloy, cobalt-chrome, polyether ether ketone (PEEK), a carbon fiber/PEEK combination, or any suitable material that is able to withstand the biomechanical stresses under which they will be placed.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A spine stabilization and fusion system comprising:
   a lateral cage configured to be placed between an upper vertebra and a lower vertebra, wherein a face of the lateral cage includes one or more first holes configured to receive fasteners and a first shaft bore configured to receive a shaft;
   a lateral block plate, wherein the lateral block plate comprises:
   one or more second holes extending from a lateral face of the lateral block plate to a medial face of the lateral block plate and configured to receive the fasteners, wherein the one or more second holes are configured to align with the one or more first holes of the lateral cage; and
   a second shaft bore configured to receive the shaft, wherein the second shaft bore is configured to align with the first shaft bore of the lateral cage;
   a lateral plate that includes one or more third holes extending from a lateral face of the lateral plate to a medial face of the lateral plate, wherein the lateral plate also includes a third shaft bore that is configured to align with the first shaft bore and the second shaft bore, wherein the lateral plate comprises a tapered waist that includes the third shaft bore; and
   an insertion handle that includes the shaft, wherein the shaft includes a threaded end, and wherein the first shaft bore and the second shaft bore are configured to temporarily receive the threaded end of the shaft of the insertion handle to facilitate placement of drilled holes into the upper vertebra and the lower vertebra, and wherein the drilled holes align with the one or more first holes of the lateral cage and the one or more second holes of the lateral block plate.

2. The spine stabilization and fusion system of claim 1, wherein the lateral block plate has an elongate body with an anterior to posterior dimension of 15 millimeters (mm) -25 mm.

3. The spine stabilization and fusion system of claim 1, wherein the lateral block plate and the lateral cage have a same height, and wherein the lateral block plate is configured to rest adjacent to the lateral cage.

4. The spine stabilization and fusion system of claim 1, wherein the lateral block plate has a medial to lateral dimension of 3 mm -8 mm.

5. The spine stabilization and fusion system of claim 1, wherein the one or more first holes of the lateral cage comprise a first hole and a second hole, wherein the first hole is angled in a cephalad direction and the second hole is angled in a caudal direction such that the fasteners can be placed in endplates of upper vertebra and the lower vertebra.

6. The spine stabilization and fusion system of claim 5, wherein the one or more second holes of the lateral block plate comprise a third hole and a fourth hole, wherein the third hole is angled in the cephalad direction and the fourth hole is angled in the caudal direction such that the fasteners can be placed through the lateral block plate, through the lateral cage, and into the endplates of the upper vertebra and the lower vertebra.

7. The spine stabilization and fusion system of claim 6, wherein an angle of the first hole and the third hole is the cephalad direction is in a range of 10 degrees -25 degrees.

8. The spine stabilization and fusion system of claim 1, wherein the fasteners comprise screws, wherein a screw has a screw head and a threaded screw shaft, wherein the screw head is configured to engage the lateral block plate and the threaded screw shaft is configured to engage vertebral bone, wherein the screw is configured to pass through one of the one or more holes in the lateral cage to secure the lateral block plate to the vertebral bone and to allow for disengagement of the lateral block plate from the lateral cage so that the lateral block plate and the lateral cage can be subjected to separate biomechanical forces during patient activity.

9. The spine stabilization and fusion system of claim 1, wherein the lateral plate comprises an anterior to posterior dimension in a range of 10 mm -20 mm.

10. The spine stabilization and fusion system of claim 1, wherein the lateral plate has a medial to lateral dimension in a range of 2 mm -4mm.

11. The spine stabilization and fusion system of claim 1, wherein the third shaft bore is configured to receive a fastener to attach the lateral plate to one or more of the lateral cage via the first shaft bore and the lateral block plate via the second shaft bore, wherein the lateral plate is configured to rest lateral to a disk space into which the lateral cage is placed.

12. The spine stabilization and fusion system of claim 1, wherein the one or more third holes are configured to receive fasteners to secure the lateral plate above and below the lateral cage into the upper vertebra and the lower vertebra.

13. The spine stabilization and fusion system of claim 1, wherein the lateral plate includes flared ends that include the one or more third holes, and wherein the lateral plate is configured for placement in a straight configuration in which the flared ends do not block the one or more second holes of the lateral block plate and a rotated configuration in which the flared ends at least partially block the one or more second holes of the lateral block plate such that the fasteners are unable to back out.

* * * * *